US00PP28610P2

(12) United States Plant Patent
Sato et al.

(10) Patent No.: US PP28,610 P2
(45) Date of Patent: Nov. 7, 2017

(54) **NEW GUINEA *IMPATIENS* PLANT NAMED 'SAKIMP040'**

(50) Latin Name: ***Impatiens×hybrida* hort**
Varietal Denomination: SAKIMP040

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,131

(22) Filed: Mar. 31, 2016

(51) Int. Cl.
*A01H 5/02* (2006.01)

(52) U.S. Cl.
USPC ..... Plt./318.3

(58) Field of Classification Search
USPC ..... Plt./318.3
CPC ..... A01H 5/0261
See application file for complete search history.

*Primary Examiner* — Kent L Bell
(74) *Attorney, Agent, or Firm* — Barbara Campbell; Bethany R. Roahrig; Cochran Freund & Young, LLC

(57) ABSTRACT

An *Impatiens* plant particularly distinguished by having orange-red flowers, and a spreading habit, is disclosed.

2 Drawing Sheets

Genus and species: *Impatiens×hybrida* hort.
Variety denomination: 'SAKIMP040'.

BACKGROUND OF THE NEW PLANT

The present invention comprises a new and distinct variety of New Guinea *impatiens* plant, botanically known as *Impatiens×hybrida* hort, and referred to by the variety name 'SAKIMP040'. 'SAKIMP040' originated from a hybridization between the proprietary female *Impatiens* line 'NF-572A2' (unpatented) and the proprietary male *Impatiens* line 'NH-209-4H-3H' (unpatented) in Misato, Japan.

In April 2011, the parental lines were crossed and a population of F1 plants was created. The F1 plants were evaluated in Misato, Japan in an open-field trial. The criteria for plant selection included spreading growth habit, vigorous rooting, and bright flower color. At the completion of the trial, a single plant selection designated 'M2013-404' was selected based on the above criteria and vegetatively propagated. From June to August 2013, the selection was evaluated in an open field in Misato, Japan. Shoot-tip cuttings of the variety were shipped to Salinas, Calif. where the plants were regenerated and re-evaluated for stability of traits. 'M2013-404' was subsequently named 'SAKIMP040' and was found to reproduce true to type in successive generations of asexual propagation via vegetative shoot-tip cuttings in Salinas, Calif.

SUMMARY

The following are the most outstanding and distinguishing characteristics of this new variety when grown under normal horticultural practices in Salinas, Calif.

1. Orange-red flowers; and
2. A spreading habit.

DESCRIPTION OF THE PHOTOGRAPHS

This *Impatiens* plant is illustrated by the accompanying photographs which show the plant's overall plant habit including form, foliage, and flowers. The photographs are of a plant grown in Salinas, Calif. under greenhouse conditions. The colors shown are as true as can be reasonably obtained by conventional photographic procedures.

DESCRIPTION OF THE NEW VARIETY

Figure 1:
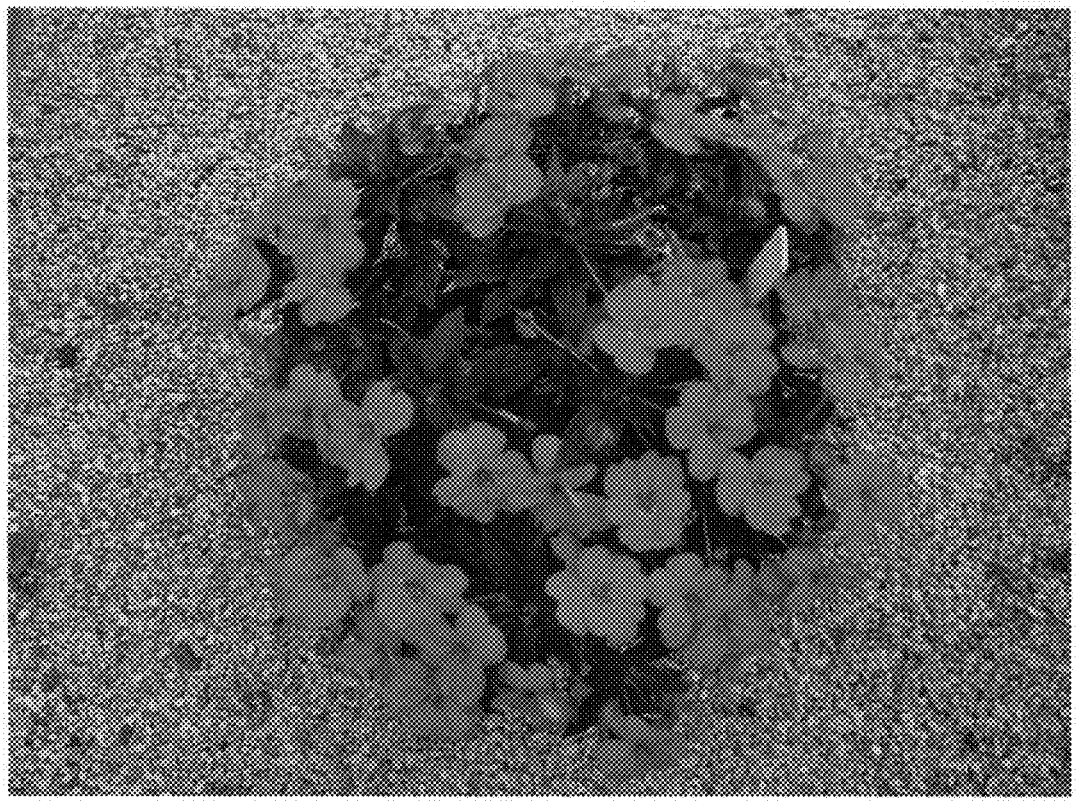
FIG. 1 shows the overall plant habit of the plant grown in a pot.
Figure 2:
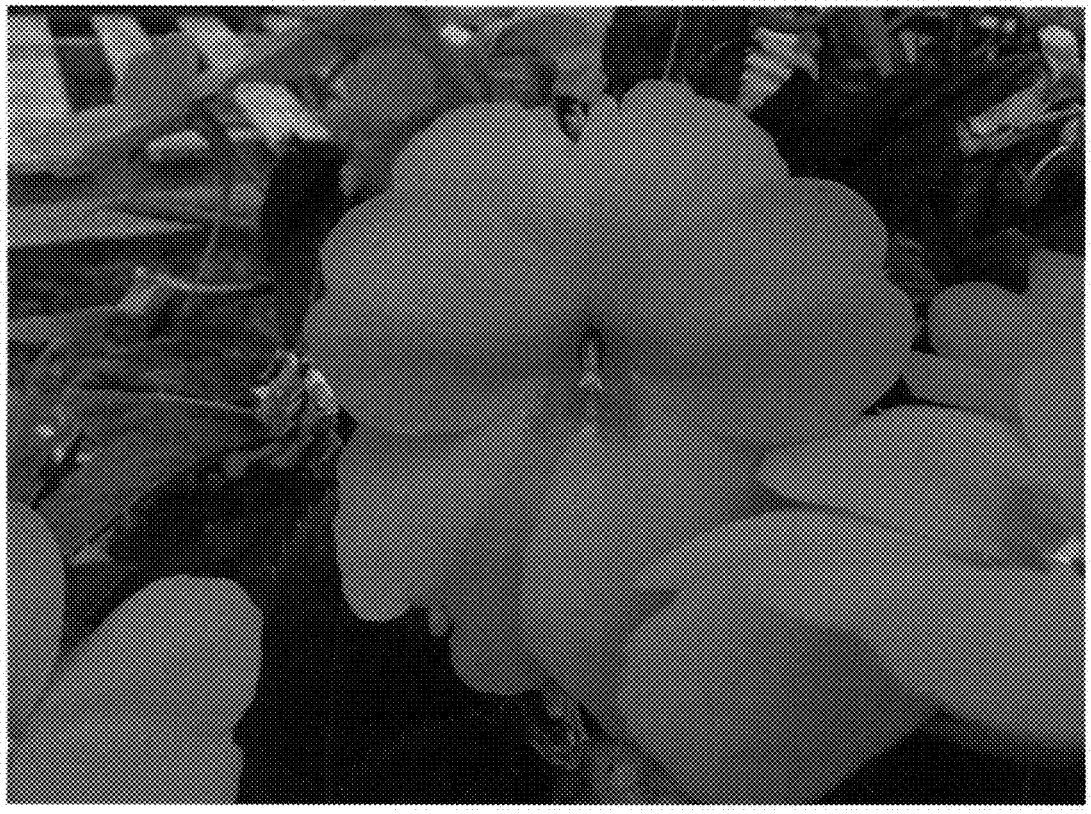
FIG. 2 shows a close-up of the mature inflorescence of the plant.

The following detailed descriptions set forth the distinctive characteristics of 'SAKIMP040'. Color references are to The Royal Horticultural Society of London Colour Chart (R.H.S.), 4$^{th}$ edition (2001). Data was obtained from plants grown about 7 months from propagation by terminal cuttings in Salinas, Calif. under greenhouse conditions. Anatomic labels are from *The Cambridge Illustrated Glossary of Botanical Terms*, by M. Hickey and C. King, Cambridge University Press.

Classification:

*Family*.—Balsaminaceae.
*Botanical*.—*Impatiens×hybrida* hort.
*Common*.—*Impatiens*.
*Designation*.—'SAKIMP040'.

Growth:

*Environmental conditions for plant growth*.—The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Parentage:

*Female parent*.—The proprietary *Impatiens* plant line 'NF-572A2'.

*Male parent*.—The proprietary *Impatiens* plant line 'NH-209-4H-3H'.

Plant description:

*Habit*.—Spreading.

*Height*.—25.0 cm from soil line to top of foliage.

*Spread*.—65.0 cm.

*Number of branches*.—32 total with 4 main branches.

*Length of branches*.—2.0 cm from soil line to first node, 7.0 cm total.

*Diameter of branches*.—3.0 cm for the main branch, 1.0 cm for the other branches.

*Color of branches*.—RHS 187A (Greyed-Purple) with slight RHS 144B (Yellow-Green).

*Life cycle*.—Annual.

*Time to produce a rooted cutting*.—About 4 weeks.

*Time to bloom from propagation*.—6 to 8 weeks.

*Flowering requirements* (*season*).—Will flower so long as temperature is above 5° C.

*Temperature tolerances*.—Plants observed to continue flowering in a temperature range of 5° C. to 36° C.

Stems:

*Stem color*.—RHS 187A (Greyed-Purple) with slight RHS 144B (Yellow-Green).

*Anthocyanin color*.—RHS 187A (Greyed-Purple).

*Stem pubescence*.—Absent.

*Stem description*.—Strong; circular cross-section, smooth and shiny.

*Stem length*.—5.0 cm from the first to the second node, 14.5 cm total.

*Stem diameter*.—6.0 cm.

*Internode length*.—4.0 to 8.0 cm.

Leaves:

*Leaf arrangement*.—Whorled with up to 5 leaves per node, opposite if only two leaves at one node.

*Leaf shape*.—Lanceolate, curled.

*Leaf tip*.—Acuminate.

*Leaf base*.—Shortly attenuate.

*Leaf margin*.—Serrate.

*Leaf surface*.—Dull; waxy.

*Leaf length*.—8.4 cm.

*Leaf width*.—3.6 cm.

*Leaf color*.—Upper surface: RHS 147A (Yellow-Green). Lower surface: RHS 147B (Yellow-Green).

*Leaf variegation*.—Absent.

*Leaf fragrance*.—Absent.

*Leaf surface pubescence*.—Absent.

*Petiole length*.—1.7 cm.

*Petiole diameter*.—0.3 cm to 0.4 cm.

*Petiole color*.—RHS 187C (Greyed-Purple) with slight RHS 144C (Yellow-Green).

*Petiole texture*.—Smooth, glabrous.

*Venation pattern*.—Pinnate.

*Venation color*.—Upper surface: Closest to RHS 139D (Green). Lower surface: Closest to RHS 139D (Green).

Flowers:

*Number of flowers per node*.—1 to 3 in bloom at one time; about 10 flower buds.

*Number of flowers per plant*.—Approximately 120 in bloom.

*Lastingness of individual blooms on the plant*.—14 days.

*Flower type*.—Single flower with spur.

*Fragrance*.—Absent.

Corolla:

*Corolla shape*.—Roughly circular with 5 radial petals.

*Corolla diameter*.—5.0 cm.

*Corolla depth*.—1.0 cm.

*Petals*.—Petal pubescence: Glabrous. Petal length: 3.8 cm. Petal width: 2.5 cm. Petal shape: Obcordate. Petal apex: Emarginate (cleaved). Petal margin: Entire. Petal base: Attenuate. Petal color: Upper surface: RHS N30B (Orange-Red). Lower surface: RHS N30C (Orange-Red). Eye zone: RHS 46A (Red).

Calyx:

*Sepal shape*.—Lanceolate.

*Sepal number*.—2.

*Sepal color upper*.—RHS 46C (Red) with RHS 143A (Green) at tip.

*Sepal color lower*.—RHS 46D (Red) with RHS 143A (Green) at tip.

*Sepal length*.—1.3 cm.

*Sepal diameter*.—6.0 mm.

*Sepal base*.—Subcordate.

*Sepal apex*.—Caudate.

*Sepal margin*.—Entire.

*Sepal texture*.—Glabrous.

Bud:

*Bud surface*.—Glabrous.

*Bud length*.—2.0 cm.

*Bud diameter*.—1.2 cm.

*Bud shape*.—Deltoid longitudinal cross-section.

*Bud color*.—RHS N30A (Orange-Red) with slight RHS 187A (Greyed-Purple) and RHS 141D (Green) at edge.

Peduncle:

*Peduncle length*.—3.5 cm.

*Peduncle color*.—RHS 187D (Greyed-Purple) with slight RHS 145C (Yellow-Green).

*Peduncle diameter*.—2.0 mm.

*Peduncle texture*.—Smooth, glabrous.

Spur:

*Spur color*.—RHS 58A (Red-Purple).

*Spur shape*.—Tubular; curved downward.

*Spur length*.—7.0 cm.

*Spur diameter*.—1.0 mm to 2.0 mm.

Reproductive organs:

*Stamen form*.—Fused; split into 4 lobes.

*Stamen number*.—5.

*Filament*.—Free.

*Anther length*.—8.0 mm.

*Anther color*.—RHS 46D (Red).

*Pistil number*.—1.

*Stigma color*.—RHS 145D (Yellow-Green).

*Style color*.—RHS 143A (Green).

*Ovary arrangement*.—Parietal.

*Ovary surface color*.—RHS 154C (Yellow-Green).

*Pollen amount*.—Abundant.

*Pollen color*.—RHS 158A (Yellow-White).

*Pollen description*.—Powdery.

*Seed production*.—Not observed.

Disease and insect resistance: No particular resistance or susceptibility observed.

COMPARISON WITH PARENTAL LINES AND COMMERCIAL VARIETY

'SAKIMP040' is distinguished from its parents as shown in Table 1 below:

TABLE 1

Comparison with Parental Lines

| Characteristic | 'SAKIMP040' | Female Parent 'NF-572A2' | Male Parent 'NH-209-4H-3H' |
|---|---|---|---|
| Flower color | Orange-red | Orange | Red |
| Plant growth habit | Spreading | Mounding | Mounding |

When 'SAKIMP040' compared to the commercial *Impatiens* variety 'SAKIMP011' (U.S. Plant Pat. No. 19,498), the following differences are as described in Table 2 below.

TABLE 2

Comparison with Similar Variety

| Characteristic | 'SAKIMP040' | 'SAKIMPOW' |
|---|---|---|
| Growth habit | Spreading | Compact |
| Petal color, upper surface | RHS N30B (Orange-Red) | RHS 44B (Red) |
| Petal color, lower surface | RHS N30C (Orange-Red) | RHS 44C (Red) |
| Spur color | RHS 58A (Red-Purple) | RHS 44D (Red) |

We claim:

1. A new and distinct variety of New Guinea *Impatiens* plant named 'SAKIMP040' as described and illustrated herein.

* * * * *